United States Patent [19]

Finch, Jr. et al.

[11] Patent Number: 6,042,569

[45] Date of Patent: Mar. 28, 2000

[54] SUBCUTANEOUSLY IMPLANTED CANNULA AND METHODS FOR VASCULAR ACCESS

[75] Inventors: Charles D. Finch, Jr., Clinton; Hendrik K. Kuiper, Edwards, both of Miss.; Jeffrey H. Burbank, Boxford, Mass.; James M. Brugger, Newburyport, Mass.; John H. Wang, North Andover, Mass.

[73] Assignee: Vasca, Inc., Tewksbury, Mass.

[21] Appl. No.: 09/009,758

[22] Filed: Jan. 20, 1998

Related U.S. Application Data

[63] Continuation-in-part of application No. 08/724,948, Oct. 2, 1996, which is a continuation-in-part of application No. 08/539,105, Oct. 4, 1995, Pat. No. 5,807,356, which is a continuation-in-part of application No. 08/183,151, Jan. 18, 1994, Pat. No. 5,562,617.

[51] Int. Cl.[7] .................................................... A61M 5/32
[52] U.S. Cl. ............................ 604/175; 604/93; 604/537
[58] Field of Search ............................. 604/93, 175, 247, 604/256, 533, 536, 537, 538, 284

[56] References Cited

U.S. PATENT DOCUMENTS

| | | |
|---|---|---|
| 274,447 | 3/1883 | Kennish . |
| 3,331,371 | 7/1967 | Rocchi et al. . |
| 3,516,408 | 6/1970 | Montanti . |
| 3,826,257 | 7/1974 | Buselmeier . |
| 3,888,249 | 6/1975 | Spencer . |
| 4,108,173 | 8/1978 | Slivenko et al. . |
| 4,405,319 | 9/1983 | Cosentino ............................ 604/175 |
| 4,405,320 | 9/1983 | Cracauer et al. ..................... 604/175 |
| 4,417,888 | 11/1983 | Cosentino et al. . |
| 4,421,507 | 12/1983 | Bokros ............................ 604/175 X |
| 4,484,912 | 11/1984 | Raible . |
| 4,496,350 | 1/1985 | Cosentino ............................ 604/175 |
| 4,543,088 | 9/1985 | Bootman et al. . |
| 4,549,879 | 10/1985 | Groshong et al. . |
| 4,610,670 | 9/1986 | Spencer ................................... 604/29 |
| 4,634,422 | 1/1987 | Kantrowitz et al. . |
| 4,639,247 | 1/1987 | Bokros . |
| 4,657,536 | 4/1987 | Dorman . |
| 4,671,796 | 6/1987 | Groshong et al. . |
| 4,673,394 | 6/1987 | Fenton, Jr. et al. . |
| 4,685,905 | 8/1987 | Janneret nee Aab . |
| 4,692,146 | 9/1987 | Hilger . |
| 4,695,273 | 9/1987 | Brown . |
| 4,701,166 | 10/1987 | Groshong et al. . |
| 4,704,103 | 11/1987 | Stober et al. . |
| 4,705,501 | 11/1987 | Wigness et al. . |
| 4,759,752 | 7/1988 | Stober . |
| 4,772,270 | 9/1988 | Wiita et al. . |
| 4,802,885 | 2/1989 | Weeks et al. . |

(List continued on next page.)

FOREIGN PATENT DOCUMENTS 2616667  6/1987  France .

*Primary Examiner*—Wynn Wood Coggins
*Assistant Examiner*—Anh-Tuan T. Nguyen
*Attorney, Agent, or Firm*—Townsend and Townsend and Crew CLLP

[57] ABSTRACT

A catheter with valve for implantation in a vascular structure of a living being. The catheter is in the general shape of a "T" with the top of the "T" implanted within the lumen of or anastomotically attached to a vascular structure. The lumen of the implanted portion of the catheter completely occupies or may be aligned with the lumen of the vascular structure, causing all blood flow through the vascular structure to be directed through the implanted portion of the catheter. A valve is placed in the wall of the implanted portion of the catheter which opens into the lumen of the leg of the "T" of the catheter upon application of sufficient differential pressure between the lumens of the two portions of the catheter. The leg of the "T" may be connected to the side wall of the implant portion of the catheter at an angle, such that the axis of the lumen of the leg of the "T" intersects the axis of the lumen of the implanted portion of the catheter at approximately a 45° angle.

15 Claims, 10 Drawing Sheets

U.S. PATENT DOCUMENTS

| | | |
|---|---|---|
| 4,822,341 | 4/1989 | Colone .................................... 604/175 |
| 4,846,806 | 7/1989 | Wigness et al. . |
| 4,892,518 | 1/1990 | Cupp et al. . |
| 4,973,319 | 11/1990 | Melsky . |
| 5,030,210 | 7/1991 | Alchas . |
| 5,041,098 | 8/1991 | Loiterman et al. . |
| 5,041,101 | 8/1991 | Seder et al. . |
| 5,053,013 | 10/1991 | Ensminger et al. . |
| 5,057,084 | 10/1991 | Ensminger et al. . |
| 5,100,392 | 3/1992 | Orth et al. . |
| 5,112,301 | 5/1992 | Fenton, Jr. et al. . |
| 5,156,600 | 10/1992 | Young . |
| 5,167,638 | 12/1992 | Felix et al. . |
| 5,169,385 | 12/1992 | Turnbull . |
| 5,176,627 | 1/1993 | Watson . |
| 5,180,365 | 1/1993 | Ensminger et al. . |
| 5,203,771 | 4/1993 | Melker et al. . |
| 5,224,938 | 7/1993 | Fenton, Jr. . |
| 5,226,879 | 7/1993 | Ensminger et al. . |
| 5,263,930 | 11/1993 | Ensminger . |
| 5,281,199 | 1/1994 | Ensminger et al. . |
| 5,290,263 | 3/1994 | Wigness et al. . |
| 5,306,255 | 4/1994 | Haindl . |
| 5,318,545 | 6/1994 | Tucker . |
| 5,324,518 | 6/1994 | Orth et al. . |
| 5,336,194 | 8/1994 | Polaschegg et al. . |
| 5,350,360 | 9/1994 | Ensminger et al. . |
| 5,350,362 | 9/1994 | Stouder, Jr. . |
| 5,360,407 | 11/1994 | Leonard . |
| 5,399,168 | 3/1995 | Wadsworth, Jr. et al. . |
| 5,409,463 | 4/1995 | Thomas et al. . |
| 5,417,656 | 5/1995 | Ensminger et al. . |
| 5,443,497 | 8/1995 | Venbrux . |
| 5,476,451 | 12/1995 | Ensminger et al. . |
| 5,503,630 | 4/1996 | Ensminger et al. . |
| 5,512,043 | 4/1996 | Verkaart . |
| 5,520,643 | 5/1996 | Ensminger et al. . |
| 5,527,277 | 6/1996 | Ensminger et al. . |
| 5,527,278 | 6/1996 | Ensminger et al. . |
| 5,562,617 | 10/1996 | Finch, Jr. et al. . |

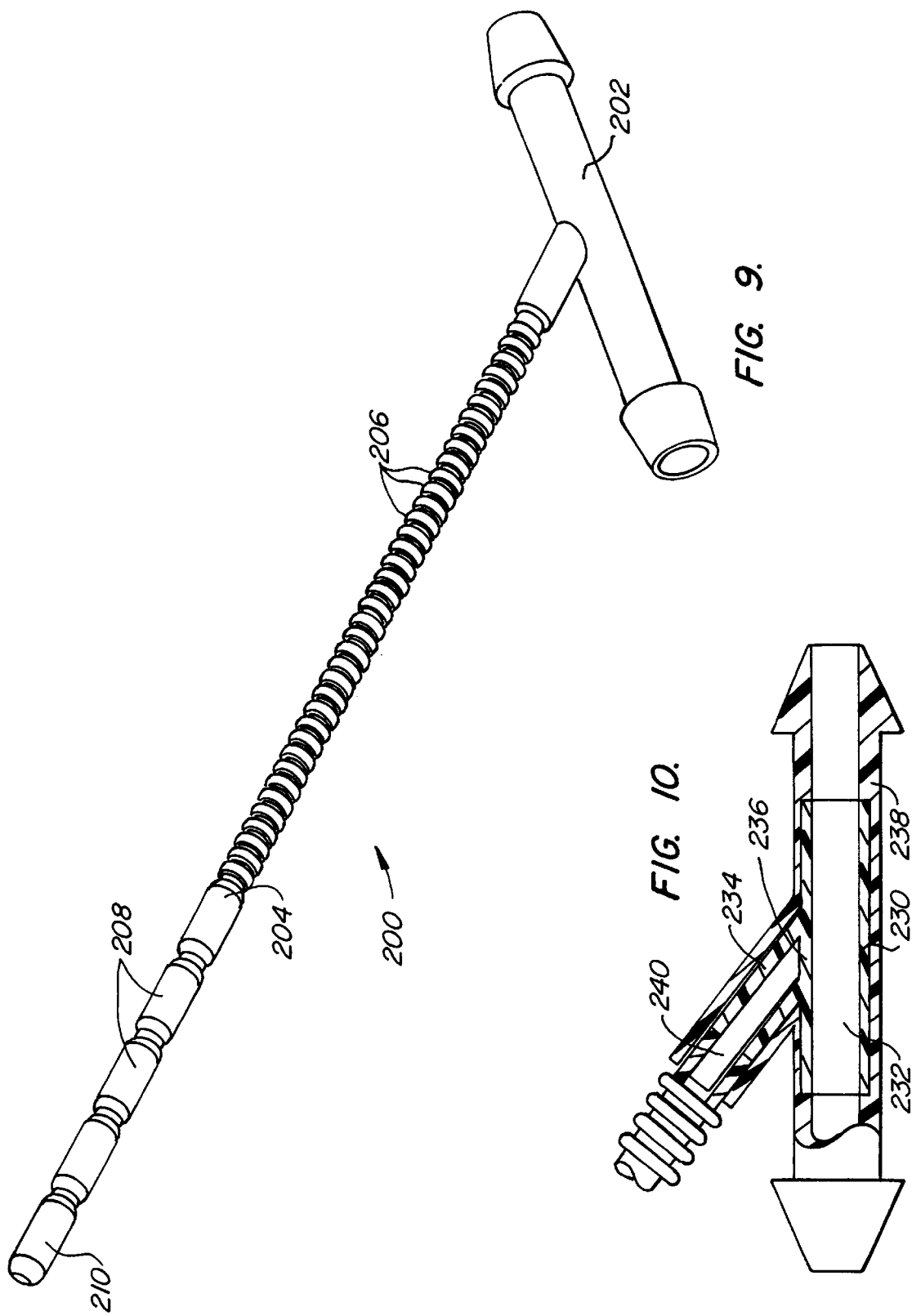

SUBCUTANEOUSLY IMPLANTED CANNULA AND METHODS FOR VASCULAR ACCESS

The present application is a continuation-in-part of application Ser. No. 08/724,948, filed on Oct. 2, 1996, which was a continuation-in-part of application Ser. No. 08/539,105, filed on Oct. 4, 1995, now U.S. Pat. No. 5,807,356 which was a continuation-in-part of application Ser. No. 08/183,151, filed on Jan. 18, 1994, now U.S. Pat. No. 5,562,617, the full disclosures of which are incorporated herein by reference.

BACKGROUND OF THE INVENTION

1. The Field of Invention

The present invention relates to subcutaneously implanted cannulas used to access the body's circulation. More particularly, this invention provides a cannula and method for establishing intermittent vascular access using an implanted cannula in the general shape of a "T".

The advent of hemodialysis for the treatment of end-stage renal disease has prompted the development of many vascular access devices for the purpose of acquiring and returning large quantities of blood for passage through an extra-corporeal circuit during hemodialysis procedure. Available devices have generally relied on the use of either indwelling venous catheters or flow through shunt devices which create an artificial fistula between an artery and vein.

Venous catheters are limited by relatively poor draw flows and by their tendency to be irritative resulting in vessel stenosis, thrombosis, and occasionally vessel perforation. They frequently fail because of infection, weakness in the vessel wall, poor catheter position, and/or thrombus formation in the catheter lumen. Shunt devices which create a fistulous blood flow between an artery and a vein have been the mainstay of modern vascular access for dialysis but are similarly problematic. Installation of these "shunts" is an extensive surgical procedure resulting in significant tissue trauma and pain. Once in place, the shunts result in additional cardiac output needs with as much as one-fifth of the cardiac output (approximately 1000 ml per minute) required for adequate function. In addition, the transfer of the arterial pressure wave results in damage to the vein at the point of anastomosis with the shunt and can result in intimal hyperplasia and subsequent thrombosis and shunt occlusion. When such occlusion occurs, another vein segment must be used for shunt revision, and exhaustion of available sites is distressingly common and can be fatal. Repeated punctures of the wall of the shunt often result in eventual failure and require additional surgery to repair or replace the shunt. The expense in terms of both health care dollars and human misery is enormous.

Each of the available access technologies mentioned thus far are also complicated by the possibility of recirculation of blood already passed through the extra-corporeal circuit resulting in the loss of treatment efficiency. The harm done to patients by the "recirculation syndrome" is insidious and at times undetected until great harm has been done.

Indwelling catheters which occupy only a portion of the vessel lumen are subject to movement within the vessel, which can cause irritation or even vessel perforation. Further, catheters which occupy only a portion of the vessel lumen, and which are inserted or threaded through the lumen for substantial distances tend to disrupt the normal flow of blood through the vascular structure, altering the hemodynamics of the blood flow in a manner which can damage the vessel, the components of the blood, and which can encourage thrombosis. Such catheters are generally unsuitable for long term implantation in arteries.

What is needed is a cannula which can be implanted within or otherwise attached to a blood vessel, which causes minimal disruption of blood flow through the lumen of the blood vessel during use and nonuse of the cannula, which does not cause vessel stenosis, thrombosis, or vessel perforation, which is capable of handling large quantities of blood, and which will retain its usefulness for a long period of time after implantation.

2. Description of the Background Art

Vascular access employing indwelling catheters is described in a number of patents and publications including U.S. Pat. Nos. 3,888,249; 4,543,088; 4,634,422; 4,673,394; 4,685,905; 4,692,146; 4,695,273; 4,704,103; 4,705,501; 4,772,270; 4,846,806; 5,063,013; 5,057,084; 5,100,392; 5,167,638; 5,108,365; 5,226,879; 5,263,930; 5,281,199; 5,306,255; 5,318,545; 5,324,518; 5,336,194; 5,350,360; 5,360,407; 5,399,168; 5,417,656; 5,476;451; 5,503,630; 5,520,643; 5,527,277; and 5,527,278; and EP 228 532; and Wigness et al. (1982) paper entitled "Biodirectional Implantable Vascular Access Modality" presented at the Meeting of the American Society for Artificial Internal Organs, Apr. 14–16, 1982, Chicago, Ill.

Catheters having distal valves are described in a number of patents including U.S. Pat. Nos. 274,447; 3,331,371; 3,888,249; 4,549,879; 4,657,536; 4,671,796; 4,701,166; 4,705,501; 4,759,752; 4,846,806; 4,973,319; 5,030,210; 5,112,301; 5,156,600; and 5,224,938.

T-shaped catheters and cannulas for a variety of purposes, some having isolation valves, are described in U.S. Pat. Nos. 5,512,043; 5,443,497; 5,169,385; 5,041,101; 4,822,341; 4,639,247; 3,826,257; 4,421,507; and 3,516,408.

Implantable dialysis connection parts are described in a number of patents including U.S. Pat. Nos. 4,692,146; 4,892,518; 5,041,098; 5,180,365; and 5,350,360.

SUMMARY OF THE INVENTION

The present invention provides improved vascular cannulas which are particularly useful for providing long-term access to a patient's vasculature, including native arteries, native veins, and artificial arterial lumens such as an arteriovenous (AV) shunt or an arterial graft. The vascular cannulas may also be used for establishing AV shunts in between an artery and a vein. The cannulas of the present invention comprise a tubular body which is implantable within or anastomotically attachable to a blood vessel and an access leg having one end attached to a side wall of the tubular body. Both the tubular body and the access leg have lumens therethrough, with the lumen of the tubular body being configured to receive at least a portion of the blood flow of a vascular lumen in which it is implanted or to which it is anastomotically attached. The access leg, which is attached to the tubular body in a generally T-shaped configuration, thus provides for access into the lumen of the tubular body for either withdrawing or returning blood (e.g. for hemodialysis or other extracorporeal treatment) or for introducing drugs or other media into the arterial or venous blood flow.

The vascular access cannula may be implanted either subcutaneously or transcutaneously. By transcutaneous, it is meant that a portion of the access leg will pass outwardly through the patient's skin to permit direct vascular access using external pumps, syringes, or other equipment. It will be appreciated, of course, that a hemostasis valve must be provided on the access leg to prevent uncontrolled blood loss. Often, any transcutaneous use of the cannula of the present invention will be only for a short time.

More usually, the cannula of the present invention will be intended for subcutaneous use. In that case, an access port is connected to the open end of the access leg and is also subcutaneously implanted beneath the patient's skin. The access port will be suitable for attachment to needles, tubes, catheters, and other devices which may be percutaneously introduced into the access port to provide a desired external connection. An example of an access port comprises a chamber having a penetrable membrane on one side thereof. Temporary access to the chamber is formed by penetrating the needle, tube, or catheter through the penetrable membrane. A preferred subcutaneous port having an internal valve is described below.

In all cases, the T-configured cannula of the present invention is an improvement over prior indwelling catheters in a number of respects. The tubular body is firmly anchored within or to the blood vessel and not subject to being moved or dislodged by blood flow. Thus, trauma to an arterial wall from movement of the cannula is significantly lessened. Moreover, by assuring that the lumen of the tubular body has a cross-sectional shape and dimensions which closely match those of the arterial lumen, smooth blood flow through the cannula can be enhanced while the risk of thrombus formation is substantially reduced.

In a preferred construction, the vascular cannula will include an isolation valve, at or near the junction between the access leg and the tubular body. The isolation valve can be any type of pressure-responsive valve that closes or inhibits flow between the tubular body lumen and the access leg lumen in the absence of a pressure drop therebetween. Thus, when blood is not being withdrawn or returned and/or when drugs or other media are not being introduced, the isolation valve will close and isolate the lumen of the access leg from arterial blood flow. Such isolation is a significant advantage since it reduces the risk of thrombus formation within the access leg and thrombus release into the arterial lumen.

Often, it will be desirable to flush the lumen of the access leg with an anti-coagulant fluid after each use. The removal of static blood and the placement of the anti-coagulant fluid further decreases the risk of thrombus formation and release. The isolation valve may be in a variety of forms, including slit valves, flap valves, ball valves, and may further be configured to provide for one-way or bi-direction flow. For example, in the case of arterial cannulas used for withdrawing blood, it may be advantageous to have a one-way isolation valve which permits blood flow from the tubular body into the access leg, but inhibits reverse flow of any materials from the access leg into the lumen. In the case of drug and other infusions into an artery or vein, it may be desirable to provide a one-way isolation valve which permits such introduction, but prevents reflux of blood into the access leg. A particularly preferred valve is a slit valve formed adjacent to or integrally within the wall of the tubular body, as illustrated in detail hereinafter. When such a slit valve is closed, the inner profile of the tubular body lumen will be generally smooth and free from discontinuities caused by the valve.

The vascular cannula may be formed from any one or a combination of a variety of biocompatible materials. By biocompatible, it is meant that the material(s) will be suitable for a long term implantation within patient vasculature and tissue and will be free from immunogenicity and inflammatory response. Usually, the cannula will be formed in whole or in part from an organic polymer, such as silicone rubber, polyethylenes, polyurethanes, polyvinylchloride, polytetrafluoroethylene (PTFE), polysulfone, or the like. Portions of the cannula may be reinforced, for example the access leg may include circumferential reinforcement to enhance its hoop strength without significantly diminishing flexibility. Such reinforcement may take the form of a helical wire or ribbon, axially spaced-apart hoops, or the like. Preferably, the reinforcement may be achieved by molding the access leg to incorporate circumferential corrugation, i.e. a plurality of axially spaced-apart circumferential ribs along all or a portion of its lengths. In all cases, it is desirable that the internal lumen of the access leg and the tubular body remain as smooth as possible to avoid disturbances to blood flow.

In a first embodiment, the tubular body of the vascular cannula will have dimensions compatible with implantation within a variety of the lumens of arteries and veins, including both native (natural) arteries and native (natural) veins, and implanted synthetic arteries. The most common native arteries in which the cannulas may be implanted include the proximal ulnar, proximal radial, brachial artery, axillary artery, and subclavian artery. The most common veins include the subclavian, the brachiocephalic, and the saphenous. Implanted synthetic arteries include bypasses, shunts (e.g. AV shunts), arterial grafts, and the like. Both native arteries and implanted synthetic arteries have lumens, and reference to "arterial lumens" herein is intended to refer to both such lumens.

In a second embodiment, the tubular body of the vascular cannula will be configured for anastomotic attachment to a blood vessel. In particular, each end of the tubular body will be configured to permit conventional end-to-end or end-to-side anastomotic attachment to a blood vessel by conventional techniques, including suturing, stapling, clamping, use of adhesives, and the like. When the vascular cannula is to be implanted in a blood vessel to receive the entire flow of that blood vessel therethrough, a gap will be surgically created in the blood vessel to produce opposed ends thereof. Each end of the tubular body of the cannula may then be attached to an opposed end of the blood vessel by end-to-end anastomosis. When the cannula is being implanted to create a shunt, one end of the tubular body will be attached to an artery while the other end is attached to a vein. In some instances, the ends of the tubular body will be attached to both the artery and the vein by end-to-side anastomoses to create a partial bypass flow of blood from the artery to the vein. In other instances, both the artery and the vein will be terminated and joined together by the tubular body which is attached to each by an end-to-end anastomosis.

Generally, the length of the tubular body will be in the range from 10 mm to 50 mm and the outer diameter will be in the range from 3 mm to 10 mm. The diameter of the lumen of the tubular body will generally be in the range from 1 mm to 8 mm. The access leg will usually have a length in the range from 25 mm to 700 mm and an outer diameter in the range from 3 mm to 10 mm. The lumen diameter of the access leg will generally be in the range from 2 mm to 8 mm.

In a preferred aspect of the present invention, at least a portion of the access leg of the arterial cannula will be sufficiently compliant so that substantially no forces are transmitted from the access leg back into the tubular body. For proper functioning of the arterial cannula, it is important that the tubular body remain properly aligned within the arterial lumen. This can be achieved by fabricating at least a portion of the access leg adjacent to the tubular body to have a low bending stiffness. The hoop strength of the access tube, in contrast, should remain relatively high, being at least sufficient to maintain patency of its lumen at internal pressures below −250 mmHg, preferably below −400 mmHg. Use of the helical reinforcement designs described above helps assure that the access leg can be sufficiently flexible while retaining sufficient strength.

In a first specific aspect of the present invention, a vascular cannula comprises a tubular body having a first end, a second end, and a lumen therebetween. The ends are adapted for anastomotic attachment to a blood vessel, generally as described above. A tubular access leg having a first end is connected to the tubular body, and further includes a second end, and a lumen between the first and second ends. A pressure-responsive valve is disposed at the junction, where the valve inhibits flow between the lumen of the tubular body and the lumen of the access leg in the absence of a pressure differential therebetween. The tubular body is preferably composed of a material of the type generally employed for vascular grafts and implants, such as expanded polytetrafluoroethylene (ePTFE), woven polyester (e.g. Dacron®, DuPont), expanded polyurethane, and the like. In this way, the tubular body of the vascular cannula can be implanted in a blood vessel via conventional end-to-end anastomotic techniques. The tubular access leg of the vascular cannula is preferably composed of silicone rubber, polyurethane, and the like. The valve preferably comprises a flange secured to the tubular body and a collar connected to the first end of the tubular access leg. Optionally, a rigid tubular insert may be placed within the collar of the valve element and joined to the first end of the tubular access leg.

Alternatively, the tubular body of the vascular cannula may comprise a rigid middle section and two end sections, where the end sections are adapted for anastomotic attachment to a blood vessel, typically being composed of a vascular graft material as described above. The rigid middle section will typically be composed of a metal or rigid plastic. Such a design can facilitate fabrication.

In a second aspect of the present invention, a method for implanting a vascular access cannula comprises providing a cannula having a tubular body with two ends, a tubular access leg connected to the tubular body at a junction, and a pressure-responsive valve at the junction. An implantation site is surgically exposed adjacent a blood vessel, and one end of the tubular body is anastomotically attached to the blood vessel. The second end of the tubular body is also attached to a blood vessel. In a first embodiment, the anastomotic attachment step comprises surgically creating a gap in a single blood vessel to produce opposed ends. Each end of the tubular body is then attached to an opposed end of the blood vessel by end-to-end anastomosis. In this way, the cannula is implanted within a single blood vessel to pass the entire blood flow up that vessel therethrough.

In a second embodiment, one end of the tubular body is attached to one blood vessel and the other end of the tubular body is attached to another blood vessel. The ends of the tubular body may be attached to the respective blood vessel by end-to-side anastomoses in order to create a partial shunt. Alternatively, the ends of the tubular body may be attached to terminal ends of an artery and a vein by end-to-end anastomoses to create a complete shunt.

In all such methods, the tubular access leg may be attached to an implanted port to establish a flow between the blood vessel and the port. Alternatively, the tubular access leg may be disposed transcutaneously in order to establish a transcutaneous flow path to the blood vessel.

BRIEF DESCRIPTION OF THE DRAWINGS

FIG. 9 is an isometric view of a second embodiment of an arterial cannula constructed in accordance with the principles of the present invention.

FIG. 10 is a detailed view of the tubular body of the cannula of FIG. 9 shown in partial cross-section.

DETAILED DESCRIPTION OF THE PREFERRED EMBODIMENT

Figure 1:
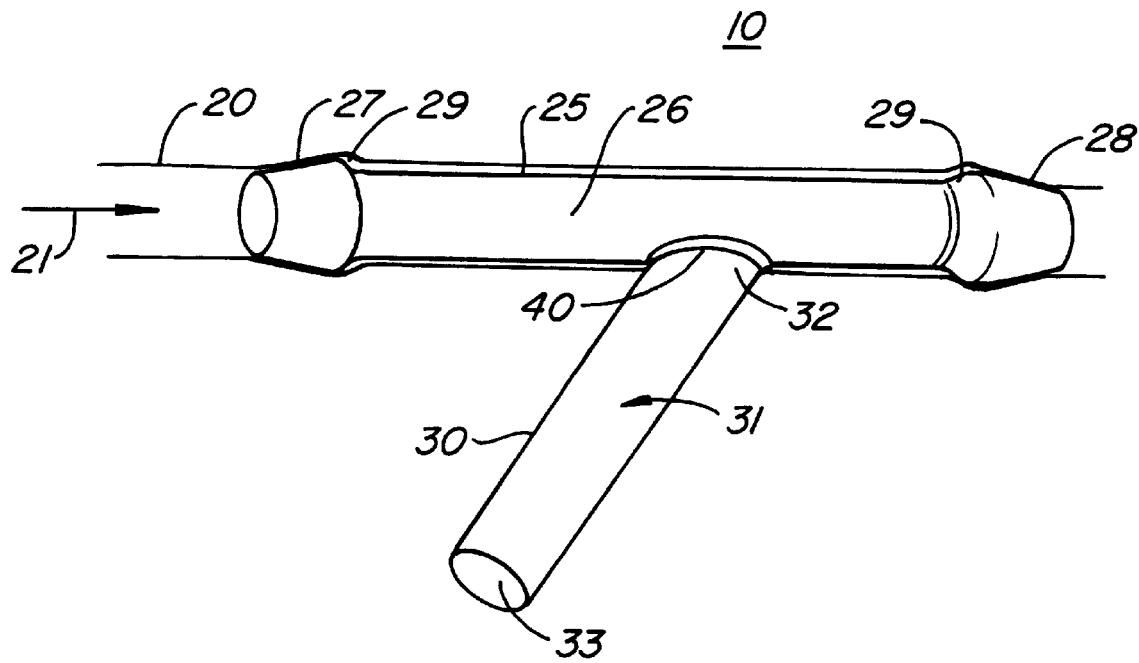
FIG. 1 shows a perspective view of the preferred embodiment of the present invention implanted within a vascular structure.

Referring to FIG. 1 there is depicted an arterial cannula 10 constructed in accordance with the principles of the present invention implanted within an arterial lumen 20. The cannula is shaped generally like a "T" and is comprised of two primary sections; the tubular body 25 and the access leg 30. The intravascular tube 25 is an elongated tube having a single lumen 26, open on both ends. When implanted within the lumen 20, the tubular body 25 will have an upstream end 27, and a downstream end 28, determined by the direction of blood flow in the vascular structure 20. In FIG. 1 the direction of blood flow is indicated by the arrow 21. The cannula however, can be implanted in either orientation.

The access leg 30 is an elongated tube having a single lumen 31. A distal end 32 of the access leg 30 is connected to the tubular body 25, generally near the mid-point thereof. The access leg 30 may extend from the tubular body 25 at any angle, including a 90° angle, but it is preferred that the access leg 30 of the cannula 10 extend from the tubular body 25 in a direction which is inclined toward the upstream end 27 of the tubular body 25. The angle formed between the access leg 30 and the upstream end 27 of the tubular body 25 is an acute angle. The angle formed between the access leg 30 and the downstream end 28 of the intravascular tube 25 is an obtuse angle. A preferred angle between the access leg 30 and the upstream end 27 of the tubular body 25 is between 30° and 60°, usually being approximately 45°.

Figure 3:
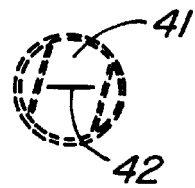
FIG. 3 shows a cross-sectional view of the valve of the preferred embodiment of the present invention in the closed position.
Figure 4:
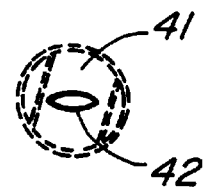
FIG. 4 shows a cross-sectional view of the valve of the preferred embodiment of the present invention in the open position.
Figure 2:
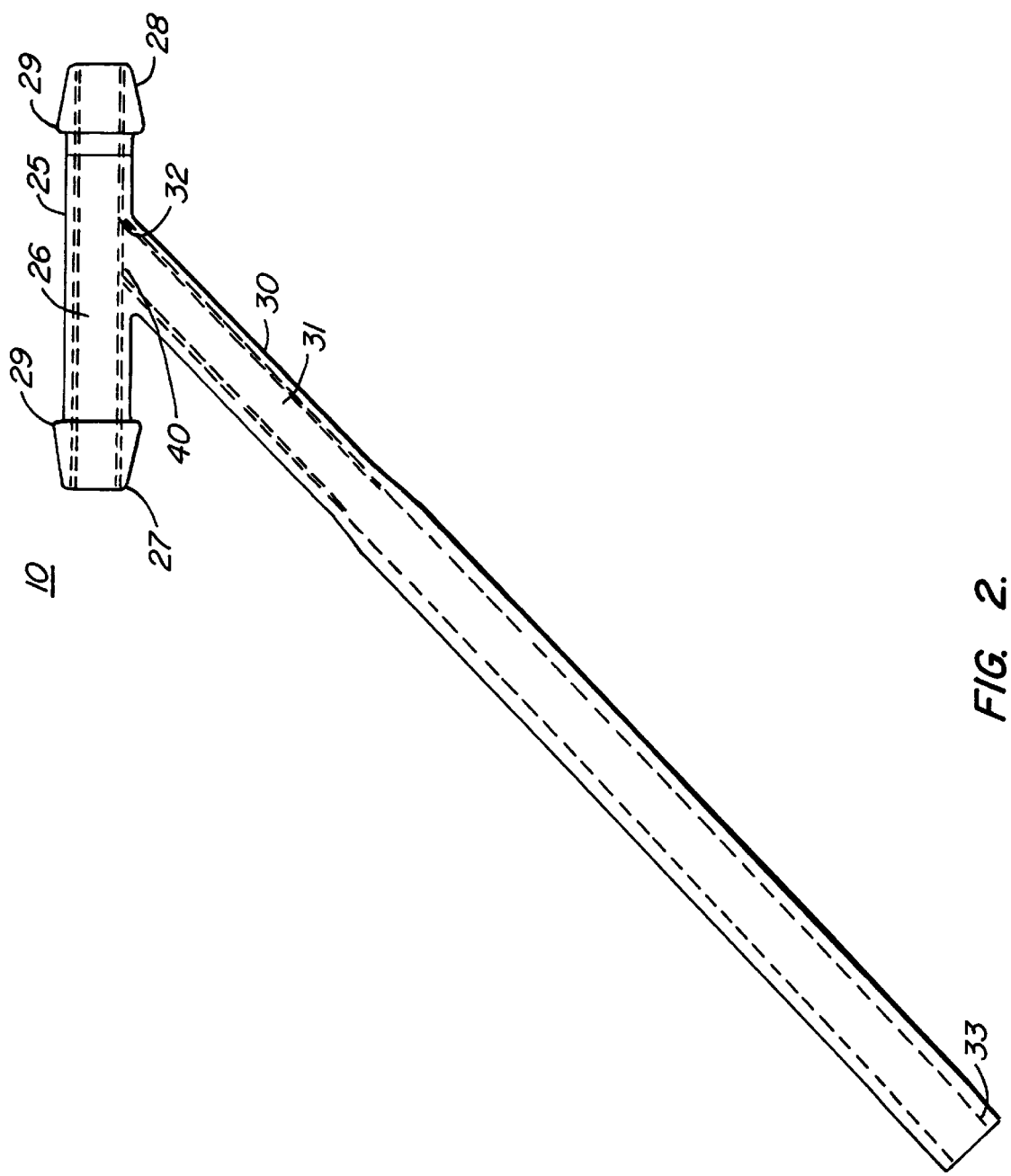
FIG. 2 shows a cross-sectional view of the preferred embodiment of the present invention.
Figure 5:
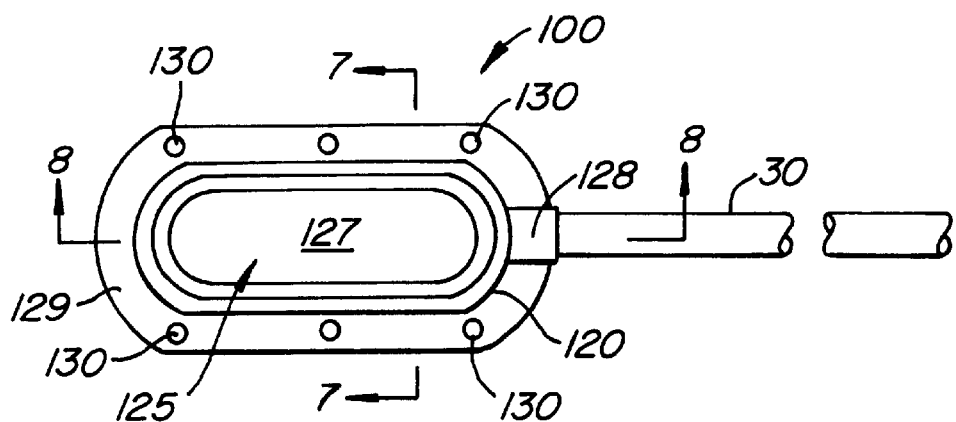
FIGS. 5 and 6 are top and side elevational views, respectively, of a percutaneous access port which may be utilized with either the arterial cannula or venous cannula of the present invention.
Figure 6:
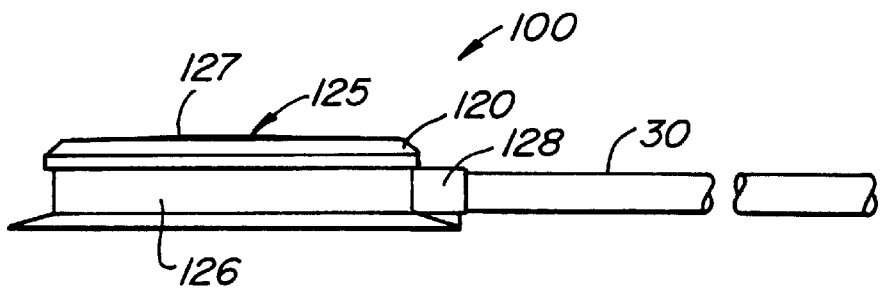
Figure 7:
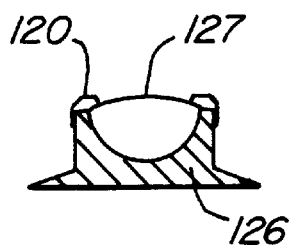
FIG. 7 is a cross-sectional view taken along line 7—7 of FIG. 5.
Figure 8:
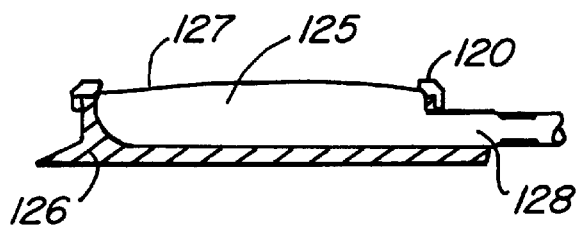
FIG. 8 is a cross-sectional view taken along line 8—8 of FIG. 5.

A valve 40 is preferably located at the point of connection between the distal end 32 of the access leg 30 and the tubular body 25. The preferred valve 40 is a slit valve. Such valves are well known in the art. As best shown in FIG. 3, the slit valve is comprised of a membrane 41 which has a slit 42 extending partially across the membrane 41 and completely through the membrane 41. The membrane 41 acts to prevent fluid flow through the lumen 31 of the access leg 30, except when adequate differential pressure exists on opposite sides of the membrane 41 to cause the slit 42 to open, as is shown in FIG. 4. The membrane 41 is located such that the side of the membrane 41 located towards the vascular structure is essentially flush with the inner wall of the intravascular tube 25. When the catheter 10 is not in use, the membrane 41 of the valve 40 and the inner surface of the tubular body 25 form a continuous tube that has minimal impact on normal blood flow through the arterial lumen.

In the preferred embodiment, the membrane 41 is comprised of a portion of the side wall of the tubular body 25. To create the valve 40, a slit 42 is cut in the side wall of the tubular body 25 to correspond to the point of connection of the access leg 30. In this manner, when the valve is closed, the inner surface of the tubular body 25 is a continuous smooth surface which has minimal impact on normal blood flow. When the valve 40 opens, fluid flow between the lumen 31 and the access leg 30 and the lumen 26 of the intravascular tube 25 occurs.

The outer circumference of the tubular body 25 is provided with expanded barbs 29 to hold cannula 10 in place within the vascular structure 20. One each of these expanded barbs 29 may be placed proximate the upstream end 27 and proximate the downstream end 28 of the tubular body 25. The expanded barbs 29 have an enlarged outer circumference which tends to slightly distend the wall of the arterial lumen 20, providing a snug fit, but not preventing the continued viability of the arterial wall. Additional areas of expanded outer diameter (not shown) may be spaced along the outer surface of the tubular body 25. The fit between the arterial wall and the tubular body 25 must be of sufficient tightness to prevent passage of blood between the arterial wall and the outer surface of the tubular body 25. Optionally, it may be possible to place ties or clamps (not shown) about the outer wall of the artery adjacent to the expanded barbs 29 to hold the cannula 10 in place. All blood flowing through the arterial lumen should pass through the lumen 26 of the tubular member 25.

In use, the proximal end 33 of the access leg 30 of the cannula 10 may be connected to a subcutaneous port, or may extend transcutaneously (i.e. through the skin). The cannula 10 is suitable for use with any device requiring or facilitating intermittent vascular access. The cannula 10 of the present invention is particularly useful for arterial access in hemodialysis, since such treatment requires large quantity blood flow, and requires relatively frequent vascular access over a long period of time. For such use two cannulas 10 may be surgically implanted. One of the devices is implanted in an artery. The other device is implanted in a vein. Usually, however, a conventional in-dwelling catheter will be used for the venous access since vein access is easer to establish. In this manner both the venous and arterial circulations are accessed separately, without fistulous communication. Current use of shunts, which create a fistulous connection between artery and vein, not only involve a more extensive surgical procedure, but are fraught with problems including increased cardiac output requirements, damage to the vein due to arterial pressure waves, and frequent shunt occlusion or thrombosis.

During hemodialysis, blood is removed from the arterial cannula 10 implanted in an artery and is subjected to the extracorporeal dialysis circuit. Removal occurs by reducing the pressure in the access leg 30 of the cannula 10, until the slit valve 40 opens, and blood flows from the tubular body 25 into the access leg 30. The treated blood is returned to a cannula implanted in a vein. At the completion of the dialysis treatment of the access leg 30 of cannula 10 is filled with anti-coagulant fluid, to discourage thrombosis and occlusion of the access legs 30. A similar process may be used for apheresis or exchange transfusion procedures. Additionally, a single arterial cannula 10 may be used for frequent administration of medication into artery or vein, or for large volume fluid infusions.

Surgical implantation of the arterial cannula 10 is a straight forward procedure. The chosen artery is located and isolated, and a small incision is made in the lumenal wall. The tubular body 25 of the cannula 10 is inserted into the incision, with the access leg 30 extending out of the lumen through the incision. The incision is then sutured to provide a snug fit around the access leg 30. The proximal end 33 of access leg 30 of the cannula 10 is then attached to a subcutaneous port (described hereinafter) or other device requiring intermittent vascular access.

Materials of construction well known in the art may be used for the manufacture of the cannula 10. However, it is important that the tubular body 25 be particularly biocompatible with the arterial wall 20, since it is intended that the wall in contact with the cannula 10 remain viable. Since the cannula 10, unlike most prior art catheters, is not designed to be pushed or threaded some distance into a blood vessel, the access tube of the cannula may be comprised of relatively flexible material. This may be accomplished by including a spring or other reinforcement element (not shown) within the walls of the cannula 10 to maintain hoop strength. The materials of construction of the tubular body should be of sufficient rigidity to maintain the preferred angle between the access leg 30 and the tubular body. The dimensions of the catheter 10 depend upon the size of the vascular structure 20 to be accessed. Typically the outer diameter of the tubular body 25 will be between 3 and 10 mm, with a wall thickness of approximately 0.5 to 1 mm, yielding a lumen 26 diameter of between 1 and 8 mm. A typical length of the tubular body 25 from upstream end 27 to downstream end 28 is between 10 and 50 mm. The maximum diameter of the outer surface of the expanded barbs 29 is approximately 30 percent greater than the diameter of the tubular body 25 where no expanded barb 29 is present. The length and flexibility of the access leg can vary depending upon the use of the catheter 10. For use with subcutaneous ports an access leg 30 length of approximately 25 mm to 700 mm, usually about 100 mm is generally sufficient.

Referring now to FIGS. 5–8, an exemplary implantable port 100 will be described. The implantable port 100 may be used with either the arterial cannula 10 described above, or with more conventional in-dwelling cannula which may be used in systems for venous access, as described in more detail hereinafter. The port 100 includes a single hematologic chamber 125, where the base and sides are formed by a circumferential wall 126. The port 100 further includes wall 126 and a cover 120 which holds a replaceable diaphragm 127 in place. The cover 120 is removable to allow replacement of the diaphragm 127 if needed. A base 129 of the port 100 comprises a flange having apertures 130 which permit fastening of the port to underlying tissue, typically using sutures. A connector 128 open to one end of the chamber 125 is connectable to the free end of access leg 30 which forms part of the arterial cannula 10 described above.

Referring now to FIGS. 9 and 10, an alternative embodiment of an arterial cannula 200 constructed in accordance with the principles of the present invention will be described. The cannula 200 includes both a tubular body 202 and an access leg 204. The access leg 204 comprises a portion adjacent to the tubular body 202 including a plurality of circumferential ribs or corrugations 206 which provides substantial hoop strength to the leg without diminishing the desired flexibility. The remainder of the access leg 204 comprises larger sections 208, with the distal end 210 being suitable for attachment to the vascular port 100 at connector 128, as described previously.

The tubular body 202 comprises a molded insert 230 including a main body portion 32 and a branch portion 234. An isolation valve 36 is formed at the end of branch 234, generally as described above with previous embodiments. Tubular body 202 is connected to the adjacent end of the access leg 206 by over molding an exterior body 238. Usually, a titanium tube 240 is placed within the junction between the end of access leg 206 and the end of branch portion 234. The tube may be titanium or other biocompatible metal. The insert 230 is typically formed from a relatively soft material, such as 40D to 50D silicone rubber. The outer portion 238 of the tubular body 202 is formed from a similar material, such as 50 D silicone rubber. The access tube may be also formed from silicone having a hardness of 40D to 50D. Conventional molding techniques may be used to form all these parts.

Figure 11:
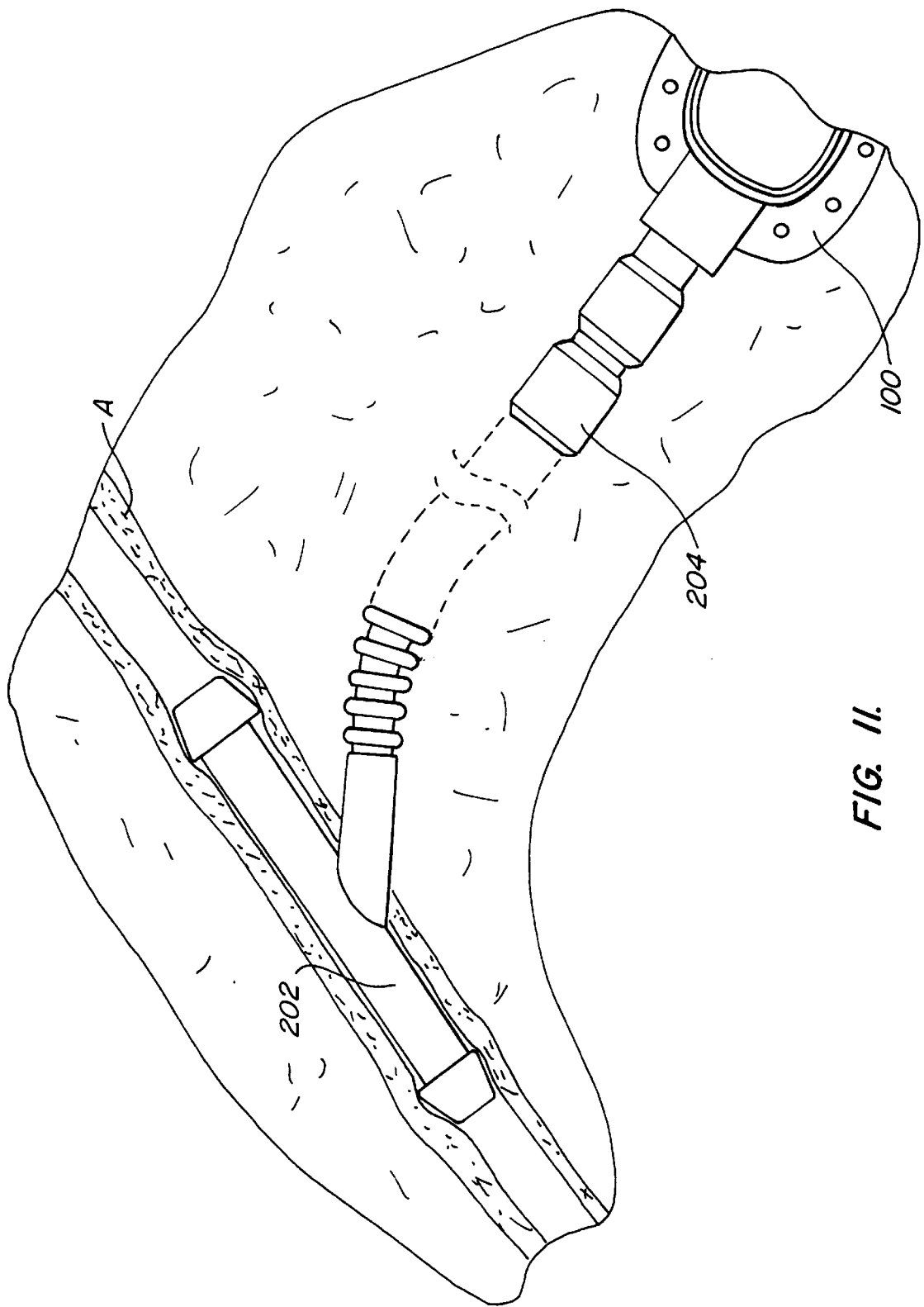
FIG. 11 illustrates subcutaneous implantation of the arterial cannula of FIG. 9 in tissue.

Referring now to FIG. 11, the tubular body 202 of the arterial cannula 200 may be implanted within an artery A by first surgically exposing the artery and thereafter forming an incision in the side of the artery. The tubular body 202 is the introduced through the incision, and the incision sutured to hold the body within the arterial lumen. The access leg 204 is then moved to a location where the arterial port 100 is to be implanted. Note that the entire assembly of the arterial cannula 200 and arterial port 100 may be implanted together within a single incision. Alternatively, the arterial cannula 200 and the arterial port 100 may be separately implanted, with the access leg 204 being separately positioned therebetween.

Figure 12:
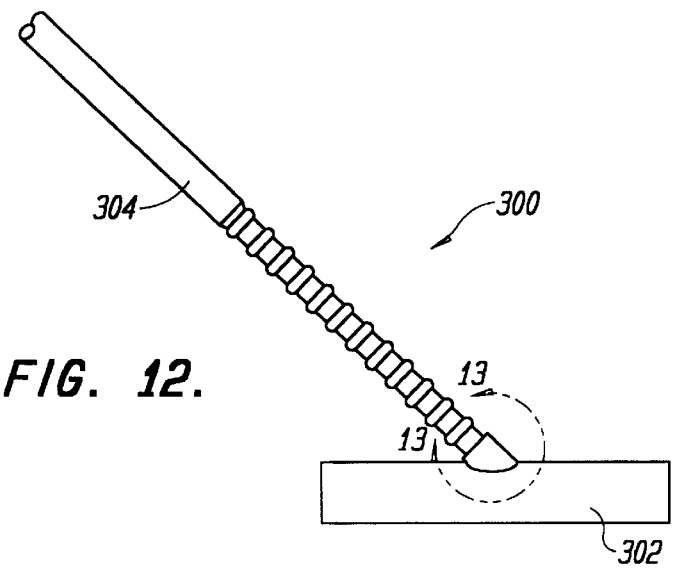
FIG. 12 is a side view of a third embodiment of a vascular cannula constructed in accordance with the principles of the present invention.
Figure 13:
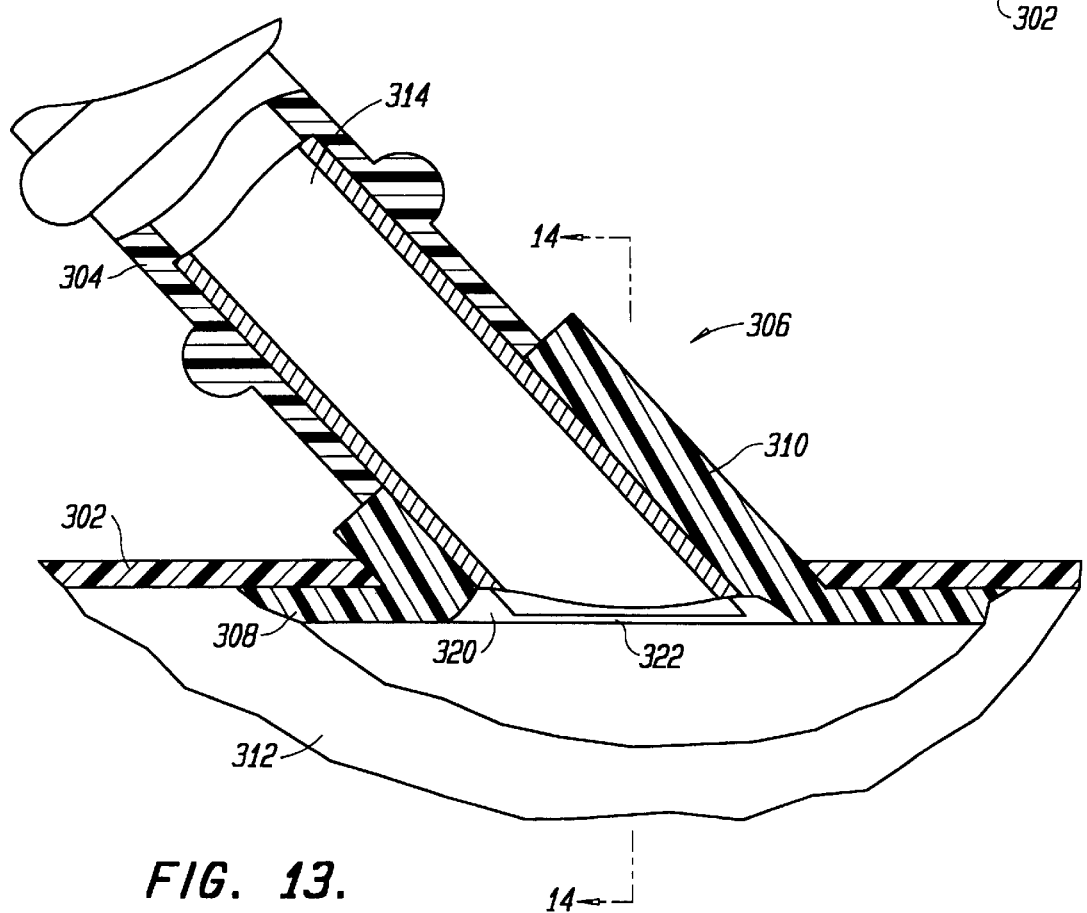
FIG. 13 is a detailed cross-sectional view taken along line 13—13 of FIG. 12, illustrating the attachment of the access leg to the tubular body in the cannula.
Figure 14:
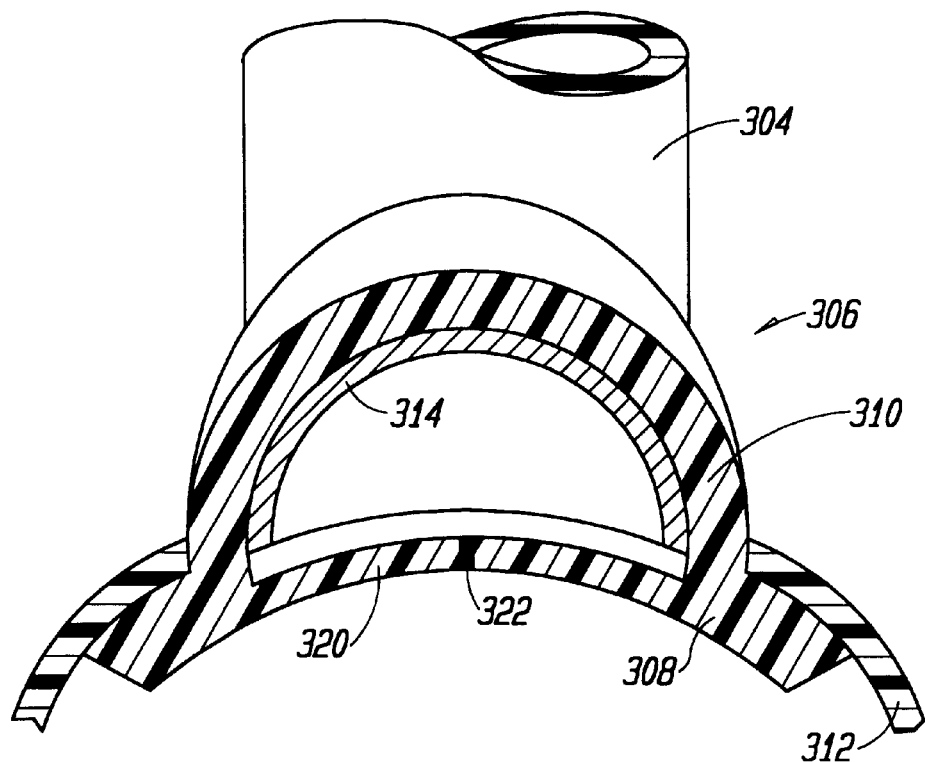
FIG. 14 is a cross-sectional view taken along line 14—14 of FIG. 13.

Referring now to FIGS. 12–14, a third embodiment of a vascular cannula 300 constructed in accordance with the principles of the present invention will be described. The cannula 300 includes both a tubular body 302 and an access leg 304. The access leg 304 is generally as described above with respect to access leg 204 in the previous embodiment. The tubular body 302, however, differs significantly from the tubular bodies described previously. In particular, tubular body 302 is intended and adapted for anastomotic attachment within a single blood vessel or between two blood vessels, typically an artery and a vein. In the embodiment of FIGS. 12–14, the tubular body 302 comprises a continuous tube formed from a single material or composite structure, where the construction and material(s) are both of type generally employed for vascular grafts and implants. The construction of vascular grafts and implants is well known and well described in patent and medical literature. See, e.g., U.S. Pat. Nos. 4,728,328; 4,731,073; 4,822,361; 4,842,575; 4,892,539; 4,955,899; and 4,957,508, the full disclosures of which are incorporated herein by reference. Preferred materials for forming the tubular body 302 include expanded polytetrafluoroethylene (ePTFE), woven polyester, expanded polyurethane, and the like.

The access leg 304 is joined to the tubular body by a valve assembly 306 including a flange 308 and a collar 310. The flange is secured to an inside surface 312 of the tubular body 302, typically by an adhesive, such as a silicone adhesive. The collar 310 extends out through an opening formed in the wall 312, preferably at an angle in the range from 30° to 90°, often from 30° to 60°, typically being 45° as illustrated. The collar 310 is attached to a lower end of the access leg 304. Conveniently, such attachment may be effected using an inner sleeve 314 which is coaxially received in the collar in the end of the access leg 304. These joints may also be formed or reinforced by an adhesive, usually a silicone adhesive. The valve assembly 306 further comprises a split-membrane valve 320 at its lower end. A split 322 extends in the axial direction of the tubular body 302 and opens and closes in response to a differential pressure across the valve.

Figure 16:
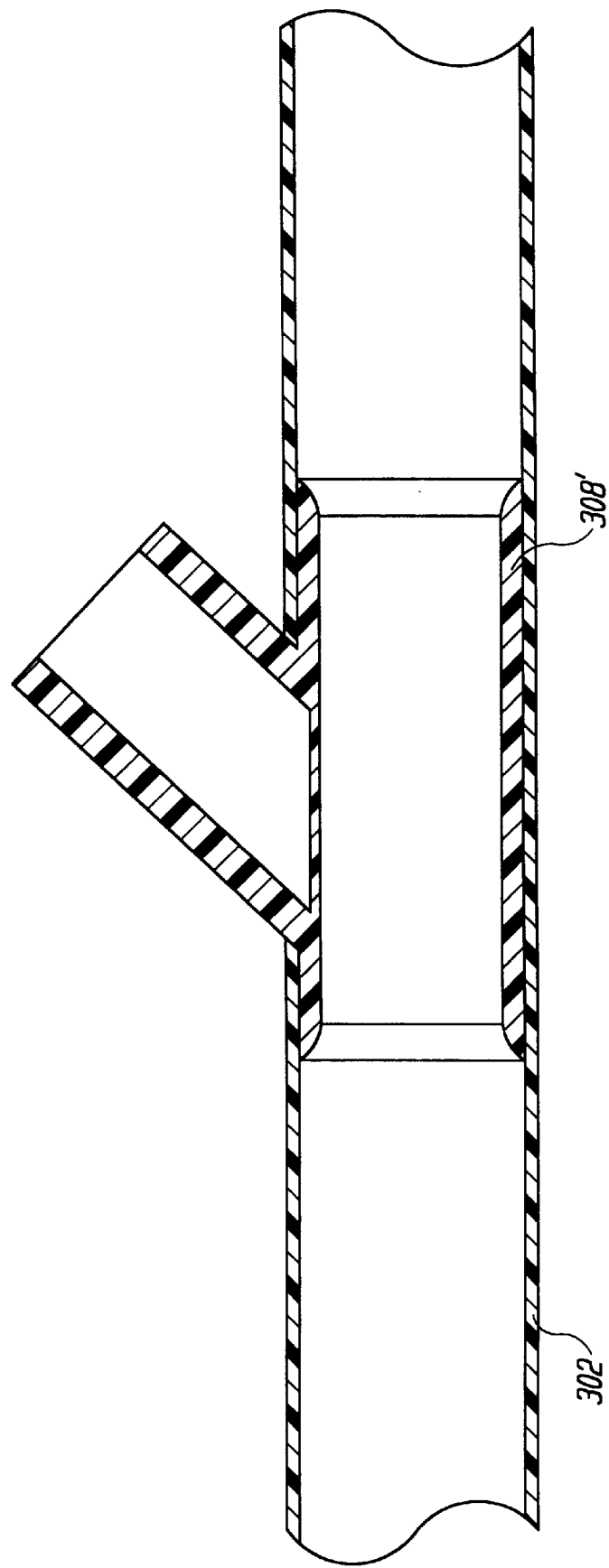
FIG. 16 is an alternative cross-sectional configuration of the vascular cannula of FIG. 12.

Referring now to FIG. 16, instead of a flange 308, as illustrated in FIGS. 13 and 14, the valve assembly 306 of vascular cannula 300 can be formed with a full tubular insert 308', as shown in FIG. 16. All other aspects of the cannula 300 would remain unchanged. Use of the tubular insert 308' is advantageous since it forms a more secure attachment to the tubular body 302. The flange construction 308, in contrast, is advantageous in that it is less restrictive to the flow lumen through tubular body 302.

Figure 15:
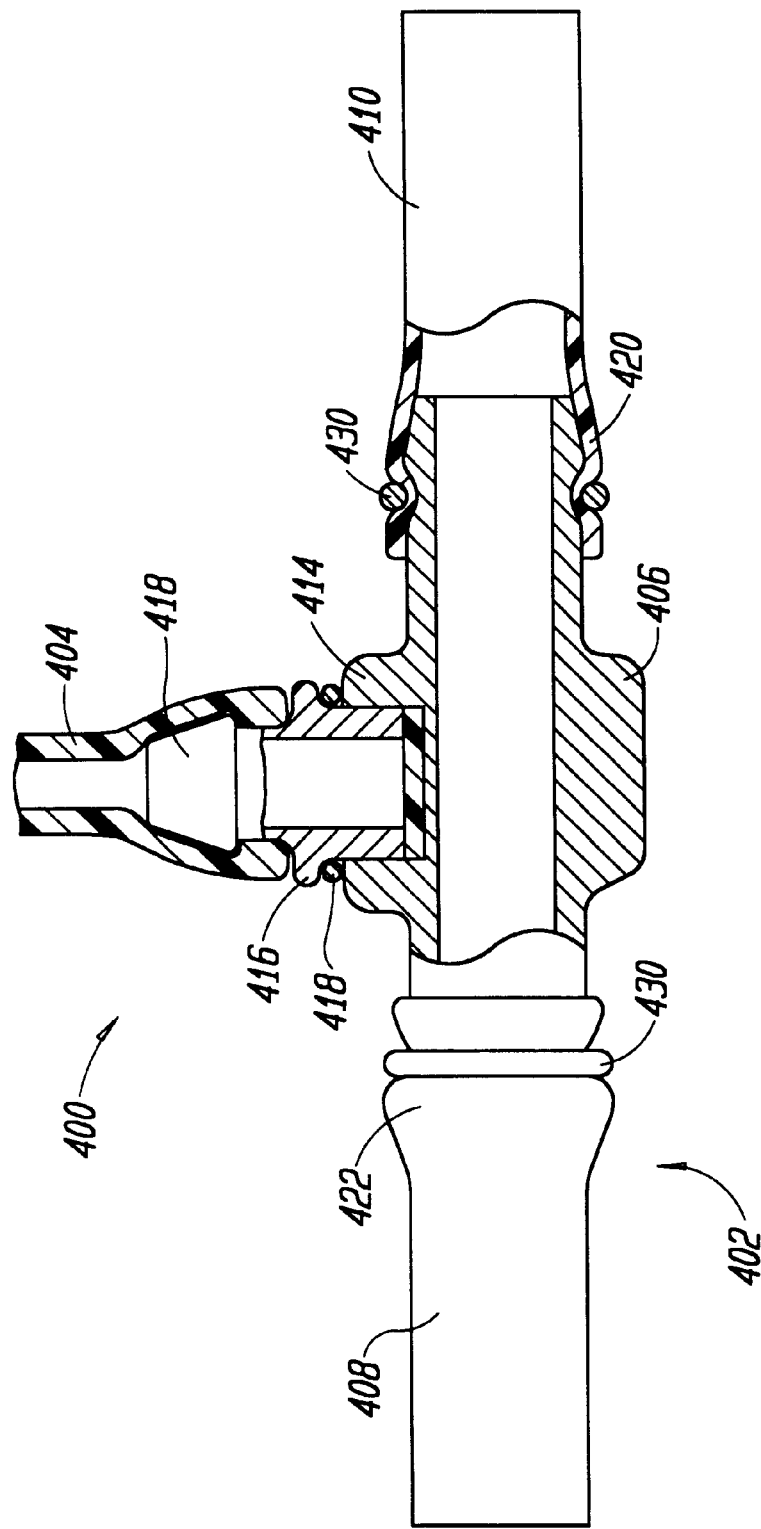
FIG. 15 is a side view of a fourth embodiment of a vascular cannula constructed in accordance with the principles of the present invention shown in partial section.

Referring now to FIG. 15, a fourth embodiment of a vascular cannula 400 constructed in accordance with the principles of the present invention will be described. The cannula 400 includes a tubular body assembly 402 and an access leg 404. The access leg 404 will generally be a silicone rubber or similar tube, generally of the type described above in connection with the previous embodiments. The tubular body assembly 402 comprises a rigid middle section 406 and two end sections 408 and 410, where the end sections are generally formed from tubular material of a type employed for fabricating vascular grafts and implants, also as described above. The rigid middle section 406 may be a hard plastic, but will usually be a biocompatible metal, such as titanium, vanadium, stainless steel, or the like. The middle section will have a silicone slit valve 412 positioned adjacent its lumen in a boss 414 formed on the side of the section. The slit valve is held in place by a male connector 416 which will usually also be composed of a metal, more usually being titanium. An O-ring 418 helps maintain the seal, and the connector 416 may be attached to the boss 414 by threading or any other conventional attachment. The access leg 404 is attached over a barb 418 formed at the upper end of the connector 416. The ends 408 and 410 are attached to barbs 420 and 422 formed at each end of the middle section 406. The attachment may be effected using an elastic ring 430 or a clamp (not shown), or any equivalent means. The remote ends 408 and 410 may be connected to a blood vessel by conventional anastomotic techniques.

Figure 17:
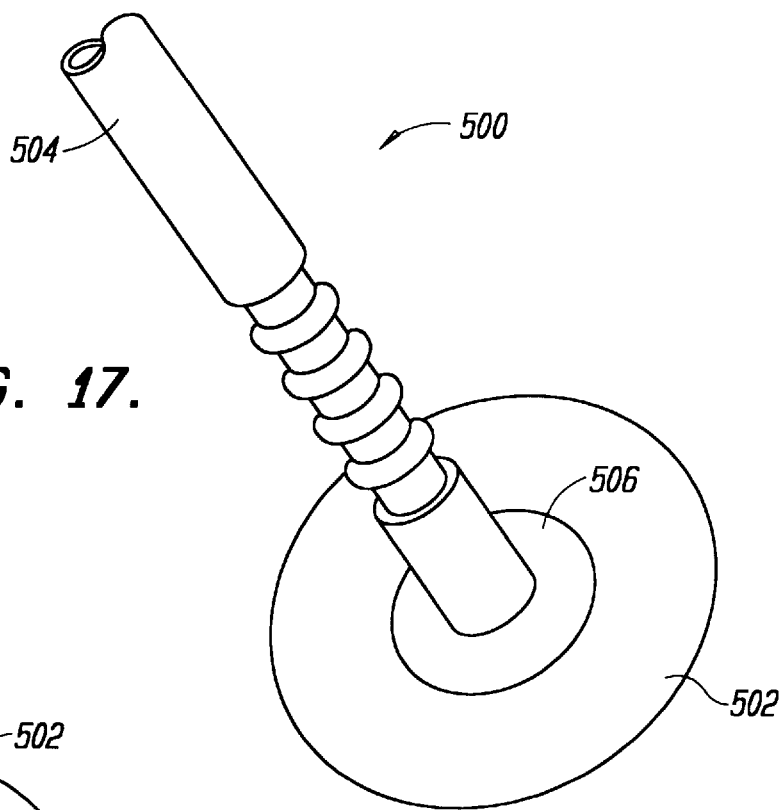
FIG. 17 is a top view of a fifth embodiment of a vascular cannula constructed in accordance with the principles of the present invention.
Figure 18:
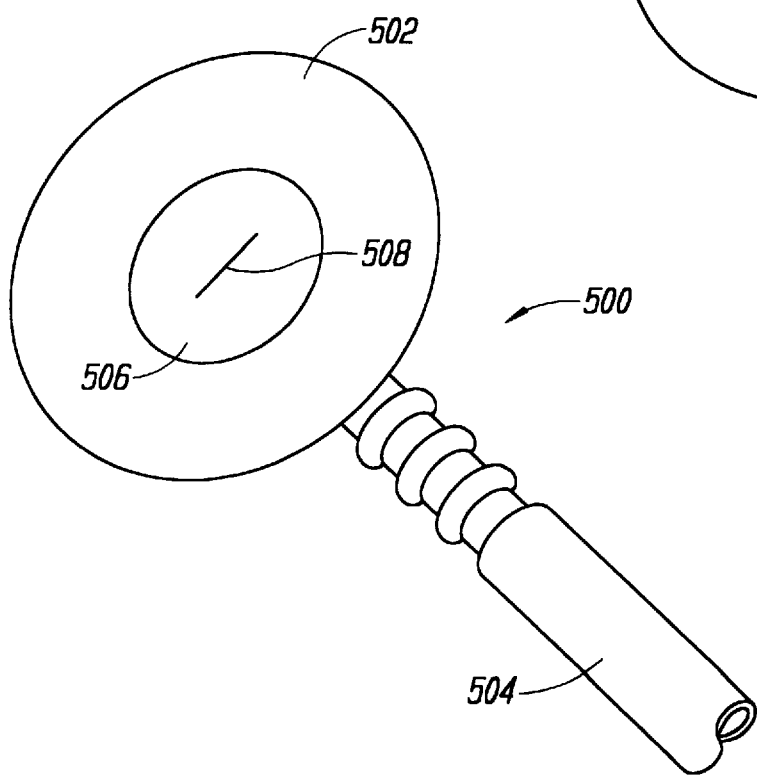
FIG. 18 is a bottom view of the vascular cannula of FIG. 17.

Referring now to FIGS. 17 and 18, a fifth embodiment of a vascular cannula 500 constructed in accordance with the principles of the present invention will be described. Instead of a tubular body, as described in previous embodiments, the cannula 500 includes a patch 502 which is used to secure the cannula to a blood vessel, typically a large vein. The patch 502 may be formed from any of the materials described above for tubular bodies, including ePTFE, woven polyester, expanded polyurethane, preferably being formed from ePTFE. An access leg 504 is constructed generally as described above for previous embodiments, except that it terminates in a small flange 506, typically having a diameter in the range from 4.5 mm to 45 mm, usually from 15 mm to 25 mm. The flange 506 comprises slit valve 508 and is attached at its periphery to an aperture formed in the patch 502. The patch 502 will be secured to the target blood vessel, typically being inserted through an incision, secured to the outside of the blood vessel, e.g. by suturing, by tissue adhesives, or the like, or sutured or otherwise secured into a region of the blood vessel which has been cut away. The slit valve 508 will thus be positioned adjacent to the blood vessel lumen, as with previous embodiments.

Although the foregoing invention has been described in some detail by way of illustration and example, for purposes of clarity of understanding, it will be obvious that certain changes and modifications may be practiced within the scope of the appended claims.

What is claimed is:

1. A vascular cannula comprising:
    a tubular access leg having a first end defining a junction, a second end, and a lumen therebetween;
    a pressure-responsive valve means at the junction which inhibits fluid flow across the valve in the absence of a pressure differential thereacross and which allows fluid flow across the valve in response to reduced pressure in the access leg without penetration of a penetration element; and
    means at the first end for positioning the junction on a blood vessel wall so that the valve is disposed adjacent to blood flowing through the vessel.

2. A vascular cannula as in claim 1, wherein the positioning means comprises one of the group consisting of (a) a tubular body having a first end, a second end, and a lumen therebetween, wherein the access leg is connected to the tubular body at the junction, (b) a patch, and (c) a suturing cuff.

3. A vascular cannula as in claim 1, wherein the tubular access leg is composed of a biocompatible elastomer selected from the group consisting of silicone rubber and polyurethane.

4. A vascular cannula as in claim 2, wherein the valve comprises a flange or tube secured to the tubular body and a collar connected to the first end of the tubular access leg.

5. A vascular cannula as in claim 4, further comprising a tubular insert connecting the collar of the valve element to the first end of the tubular access leg.

6. A vascular cannula as in claim 2, wherein the tubular body comprises a rigid middle section and two end sections, wherein said end sections are adapted for anastomotic attachment to a blood vessel.

7. A vascular cannula as in claim 6, wherein the rigid middle section is composed of a metal and said end sections are composed of a material selected from the group consisting of expanded polytetrafluoroethylene, woven polyester, and expanded polyurethane.

8. A method for implanting a vascular access cannula, said method comprising:
    providing a cannula having a flexible tubular access leg with a junction at one end, and a pressure-responsive valve at the junction;
    surgically exposing a blood vessel having blood flow therethrough; and
    attaching the junction to or between blood vessels so that the valve is disposed adjacent to the blood flow, whereby blood may be removed through the pressure-responsive valve by reducing pressure in the access leg or returned through the pressure-responsive valve by increasing pressure in the access leg.

9. A method as in claim 8, wherein the attaching step comprises (1) surgically creating a gap in a single blood vessel to produce opposed ends thereof and (2) attaching each end of a tubular body comprising the junction to one of the opposed ends by an end-to-end anastomosis.

10. A method as in claim 8, wherein the surgical attaching step comprises (1) attaching one end of a tubular body comprising the junction to one blood vessel and (2) attaching the other end of the tubular body to another blood vessel.

11. A method as in claim 10, wherein the ends of the tubular body are attached to the respective blood vessels by end-to-side anastomoses.

12. A method as in claim 10, wherein the ends of the tubular body are attached to the respective blood vessels by end-to-end anastomoses.

13. A method as in claim 8, further comprising attaching another end of the tubular access leg to an implanted port to establish a flow path between the blood vessel and the port.

14. A method as in claim 8, further comprising transcutaneously positioning the other end of the tubular access leg to establish a transcutaneous flow path to the blood vessel.

15. A method as in claim 8, wherein the junction is a patch which is attached to or within a blood vessel.

* * * * *